(12) United States Patent
Dale et al.

(10) Patent No.: US 8,417,314 B2
(45) Date of Patent: Apr. 9, 2013

(54) RUTHENIUM PURPLE BIOSENSOR

(75) Inventors: Nicholas Dale, Kenilworth (GB); Faming Tian, Coventry (GB)

(73) Assignee: University of Warwick, Coventry (GB)

(*) Notice: Subject to any disclaimer, the term of this patent is extended or adjusted under 35 U.S.C. 154(b) by 0 days.

(21) Appl. No.: 12/448,625

(22) PCT Filed: Jan. 3, 2008

(86) PCT No.: PCT/GB2008/000022
§ 371 (c)(1),
(2), (4) Date: Jan. 7, 2011

(87) PCT Pub. No.: WO2008/081193
PCT Pub. Date: Jul. 10, 2008

(65) Prior Publication Data
US 2011/0105870 A1    May 5, 2011

(30) Foreign Application Priority Data

Jan. 4, 2007    (GB) .................................. 0700157.1

(51) Int. Cl.
*G01N 27/327*    (2006.01)
(52) U.S. Cl. .................. 600/376; 600/351; 204/403.05; 204/403.04
(58) Field of Classification Search .............. 204/403.01–403.14; 600/351; 205/777.5, 778, 792
See application file for complete search history.

(56) References Cited

PUBLICATIONS

Crumbliss et al., Short Communication—"The Electrochemistry of Hexacyanoruthenate at carbon electrodes and the use of Ruthenium compounds as mediators in the Glucose/Glucose oxidase System," J. Electroanl. Chem. 206 (1986) 327-331.*
Chen et al., "Ruthenium purple-containing zeolite modified electrodes and their application for the detection of glucose," Journal of Electroanalytical Chemistry 466 (1999) 82-89.*
Garjonyte, R. et al., "*Amperometeric glucose biosensors based on Prussian Blue—and polyaniline-glucose oxidase modified electrodes*", Biosensors Bioelectronics, vol. 15, pp. 445-451 (2000).
Tian, Faming et al., "*Ruthenium Purple-Mediated Microelectrode Biosensors Based on Sol-Gel Film*", Analytical Chemistry, vol. 70, No. 17, pp. 6760-6766, (Sep. 1, 2007).
Shyu, Suh-Ching et al., "*Characterizations of Iron-Containing Clay Modified Electrodes and Their Applications for Glucose Sensing*", Journal of Electrochemical Society, vol. 145, No. 1, pp. 145-155 (Jan. 1998).
Zen, Jyh-Myng et al., "*A Clucose Biosensor Employing a Stable Artificial Peroxidase Based on Ruthenium Purple Anchore3d Cinder*", Analytical Chemistry, vol. 75, No. 11, pp. 2703-2709 (Jun. 1, 2003).

* cited by examiner

*Primary Examiner* — Alex Noguerola
(74) *Attorney, Agent, or Firm* — Wiggin and Dana LLP

(57) ABSTRACT

The invention relates to a biosensor comprising an electrically conductive substrate, with a first layer comprising Ruthenium Purple formed on the substrate, a second layer comprising polyaniline or a derivative thereof comprising one or more non-polar substituents formed on the first layer, and a third layer comprising one or more enzymes trapped within a matrix formed on the second layer. The biosensor is for use in the detection of analytes such as purines and derivatives thereof, particularly in the detection of hypoxanthine.

33 Claims, 7 Drawing Sheets

RUTHENIUM PURPLE BIOSENSOR

CROSS-REFERENCE TO RELATED APPLICATIONS

Figure 1:
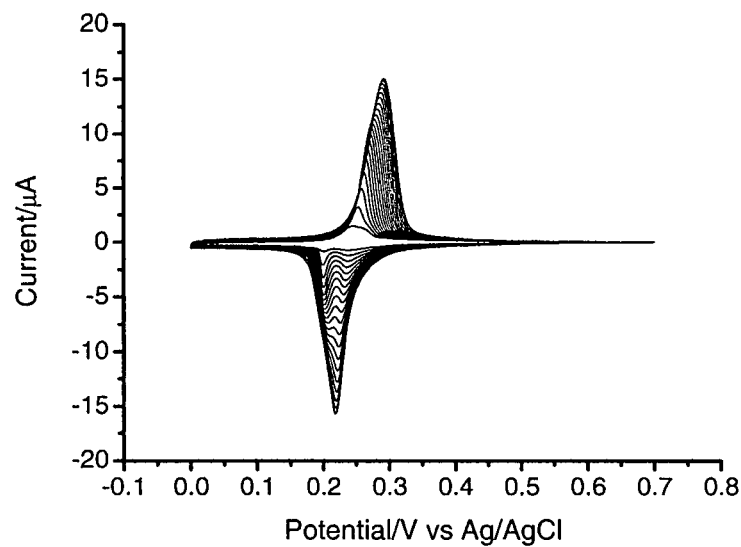

This application is a U.S. National Stage application of International Patent Application Serial No. PCT/GB2008/000022 filed Jan. 3, 2008.

The present invention relates to a biosensor, which can be used for the detection of chemicals, such as purines and derivatives thereof, for example hypoxanthine, adenosine, ATP and/or inosine. This application claims priority from GB 0700157.1, filed 4 Jan. 2007, which is incorporated herein in its entirety.

BACKGROUND OF THE INVENTION

Biosensors contain an electrode with a biorecognition molecule such as enzymes, antibodies, organelles and whole cells to allow the specific identification of analytes such as metabolytes, ions, gases and organic vapours. Such biorecognition elements are typically attached to a transducer, such as an electrochemical, piezoelectric, optoelectronic, fibreoptic, thermistor, diode or surface acoustic device, to enable the binding of the analyte to the biorecognition element to be detected. Amperometric biosensors, for example, are reviewed in the article by Palmisano F., et al. (Fresenius J. Anal. Chem. (2000), Vol. 366, pages 586-601). A wide range of mediator compounds and mediator polymers have been used to enable the transfer of electrons from a suitable biorecognition element, such as an enzyme, to an electrode.

Since the early work by Clark and Lyons (Clark and Lyons, 1962) biosensors have evolved continuously to become a powerful analytical tool in many fields. Immobilization of active enzymes central to the operation of biosensors has been achieved in many different ways (Cass, 1990). However entrapment of enzymes in electropolymer matrices (Bartlett and Cooper, 1993) has the particular advantage of producing biosensors with very small and custom shaped sensing elements. These types of micro-biosensors are ideal for detecting neurotransmitter release in the central nervous system as they are minimally invasive.

Cosnier and coworkers developed pyrrole derivatives that are suitable for entrapping enzymes on microelectrodes, and used these methods to develop a variety of biosensors including sensors sensitive to glutamate (Poitry et al., 1997) and dopamine (Cosnier et al., 1997). Indeed, biosensors using biotinised derivatives are shown in U.S. Pat. No. 6,197,881B in the name of Cosnier. Although these are important signaling agents in the nervous system, the polymer films on these sensors were insufficiently robust to survive implantation into neural tissue (Poitry et al., 1997) and the sensors had mixed success at detecting release from biological tissue (Poitry et al., 1997; Cosnier et al., 1997). Nevertheless, the methods developed by Cosnier are of potentially very general utility and the inventors have previously adapted them to construct robust and sensitive microelectrode biosensors that permit, spatially localized and fast detection of purine release from the nervous system. The purines, ATP and adenosine, perform extremely important signaling functions in both the peripheral and central nervous system. Peripherally, they are involved in the control of smooth muscle contraction and are powerful vasodilators (McMillan et al., 1999). Centrally, their diverse roles include regulation of spinal pain pathways (Sawynok, 1998), neuroprotection during ischaemia (Dale et al., 2000), control of transmitter release (Brundege and Dunwiddie, 1997), regulation of spinal motor pattern generation (Dale, 1998; Dale and Gilday, 1996) and induction of sleep (Porkka-Heiskanen, 1999). Adenosine, in particular, does not conform to the conventional paradigm of chemical neurotransmission in the nervous system. Instead of being released directly like most transmitters, adenosine is usually produced in the extracellular space from previously released ATP through the actions of special enzymes collectively known as the ectonucleotidases (Zimmermann and Braun, 1999). The production of adenosine—its spatial domains and kinetics of accumulation—are central to its function in the nervous system and can therefore be expected to differ considerably from those of conventional neurotransmitters. HPLC analysis of collected superfusate has been used to study adenosine release, however this method has very limited time and spatial resolution (Pedata et al., 1993). New methods for directly measuring adenosine production would thus be of great value in understanding its contribution to neural functions.

Recently, detection of adenosine produced during physiological activity has been achieved with an 3-enzyme biosensor (mark-1) (Dale, 1998) that utilizes a microdialysis electrode (250 mm diameter) to trap the required enzymes behind a semi-permeable membrane. This sensor is the subject of WO 99/07877 and is sensitive and has successfully detected release of adenosine from *Xenopus* embryo spinal cord (Dale, 1998) during motor activity, and mammalian hippocampus during hypoxia (Dale et al., 2000; Pearson et al., 2001). However it is too large to implant into nervous tissue without causing considerable damage and subsequent tissue reaction that may confound and invalidate physiological measurements. Furthermore the large size of the sensing assembly (500 μm when used in its finally constructed format) introduces diffusional delays which slows sensor responsiveness. To increase the range of applications for this measurement technology and to enable resolution of fast production of adenosine and related purines much smaller and faster responding biosensors are thus required.

The ability to monitor of the levels of purines such as hypoxanthine is also of vital importance in medicine. For example, hypoxanthine can provide an indicator of a baby's oxygen levels during birth and acts as an early warning system for distress.

If a baby's brain is being starved of oxygen, midwives and doctors have a more accurate idea of when a caesarean section is necessary. The ability to monitor the hypoxanthine levels can therefore help to prevent unnecessary emergency caesarean sections, as doctors sometimes perform one if they fear the baby is suffering foetal hypoxia, or oxygen starvation, which can result in cerebral palsy or other biological defects for a child. A baby with more than 5 μM of hypoxanthine per litre of blood is at a severe risk of foetal hypoxia. A level of 15 μM or more could indicate major hypoxian and a heightened risk of brain damage.

At present, blood samples are taken to a laboratory for analysis, which causes a delay in obtaining the results. It would therefore be beneficial to have a biosensor which would give doctors in the delivery room almost instant data on whether an unborn child faced the risk of hypoxia.

One alternative electrode is discussed in WO 03/087801. This discloses the use of sugar-derivatised pyrroles on a platinum or platinum-alloy substrate, in combination with a second layer comprising an ampiphilic pyrrole. This was found to improve the resilience of the sensor.

An alternative arrangement of the biosensor is shown in WO 2004/048603, which is incorporated herein by reference in its entirety. This describes methods of producing sol-gels on electrically conductive substrates. This allows the entrapment of, for example, enzymes into a sol-gel matrix for the production of biosensors.

EP 0537761 discloses a biosensor comprising an electrode on a substrate of polyethylene tetraphthalate. An enzyme, such as xanthine oxidase, is attached to an electrode via an electron acceptor, such as potassium ferricyanide, which is also known as Prussian Blue (PB).

However, the use of PB as an electron acceptor provides problems, most notably due to its intolerance to the presence of $Na^+$ ions in physiological fluids. $Na^+$ ions are prominent in physiological fluids such as blood, which clearly renders PB less suitable as a biosensor material.

It is therefore also necessary to develop a biosensor that is tolerant to the presence of $Na^+$ ions in physiological fluids and can still readily function in such environments.

A related compound to PB, Ruthenium Purple (RP), which has the formula $KFeRu(CN)_6$ or $Fe_4[Ru(CN)_6]_3$, has also been used in biosensors. However, the only RP modified biosensors which have been described in the literature to date are all related to glucose biosensors, and clay, zeolite or cinder is used to anchor the RP in those biosensor configurations (see e.g. Zen et al, Anal. Chem., 2003, 75, 2703-2709).

RP does not possess the intolerance to $Na^+$ ions that is exhibited by PB. Although the presence of $Na^+$ ions has a minor effect upon the potential, the RP still functions to an effective level as an electron acceptor. In similar environments, similar biosensors comprising PB simply cease functioning.

The above properties are illustrated in the electrochemistry. The electrochemistry of RP is largely unaffected in ordinary phosphate buffer solutions which contain significant concentrations of $Na^+$ ions (see FIG. 2). In order to maintain the electrochemical activity of PB, it is known that cations which fit the PB lattice, such as $K^+$ $Rb^+$, $Cs^+$ and $NH_4^+$, are required. Other smaller cations in a buffer solution, such as $Na^+$ $Mg^{2+}$, $H^+$ and $Ca^{2+}$, act as blocking cations, negatively affecting the electrochemistry of the PB which impacts upon the operational potential of the biosensor. Hence the use of $Na^+$ ions, which are widely employed in bioanalysis, has a significant restrictive effect upon the use of PB in biosensors.

Similarly to PB and its other analogues, RP has both soluble and insoluble forms. However, RP is considerably more soluble in water than PB, and is extremely stable in its insoluble oxidised form. At the optimum operational potential of the RP modified biosensor (which is usually 0 or −50 mV vs Ag/AgCl), RP is in its soluble form, which is susceptible to leaching, resulting in a loss of activity. A decrease in response is almost always observed in such biosensors. The ability to stabilise the RP against such leaching and boost the response would therefore be desirable.

Therefore, in accordance with the present invention, there is provided a biosensor comprising:

(i) an electrically conductive substrate;
(ii) a first layer formed on the substrate, the first layer comprising Ruthenium Purple;
(iii) a second layer formed on the first layer, the second layer comprising polyaniline or a derivative thereof comprising one or more non-polar substituents; and
(iv) a third layer formed on the second layer, the third layer comprising one or more enzymes. Preferably the enzymes are trapped within a matrix, or adsorbed onto the second layer. Most preferably a matrix is used.

In order to overcome the leaching problem associated with RP biosensors, a modified RP formation method is employed in the present invention, which has not previously been described. The present invention preferably involves stabilising the RP layer by heating, electrochemically cycling it in a solution of $RuCl_3$, and contacting it with a solution containing aniline or a derivative thereof. In this way, a membrane comprising polyaniline or a derivative thereof comprising one or more non-polar substituents is introduced into the RP modified biosensor.

Figure 4:
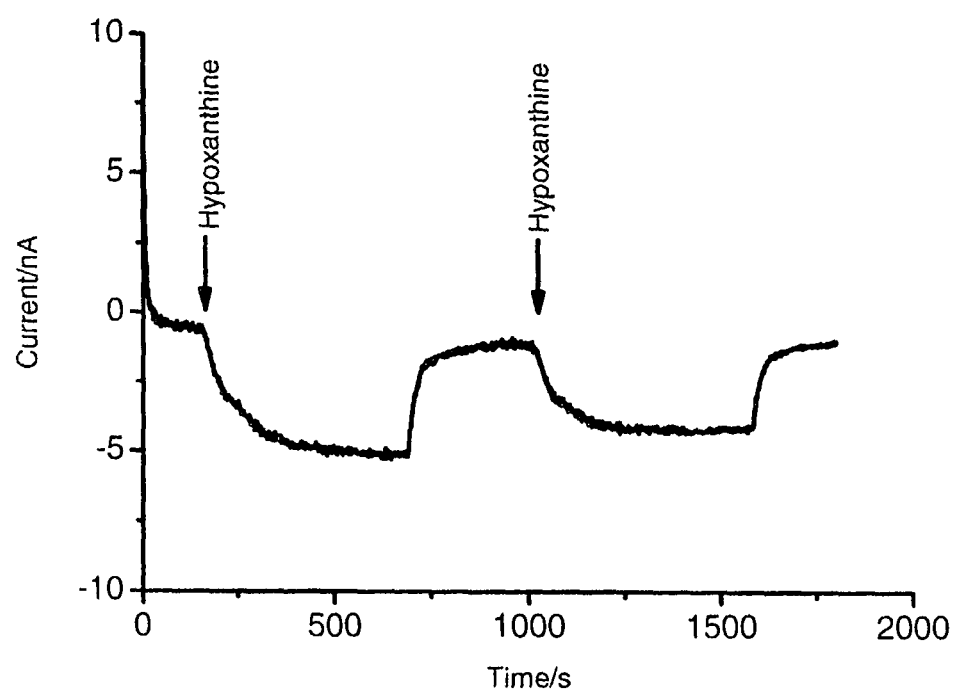
Figure 5:
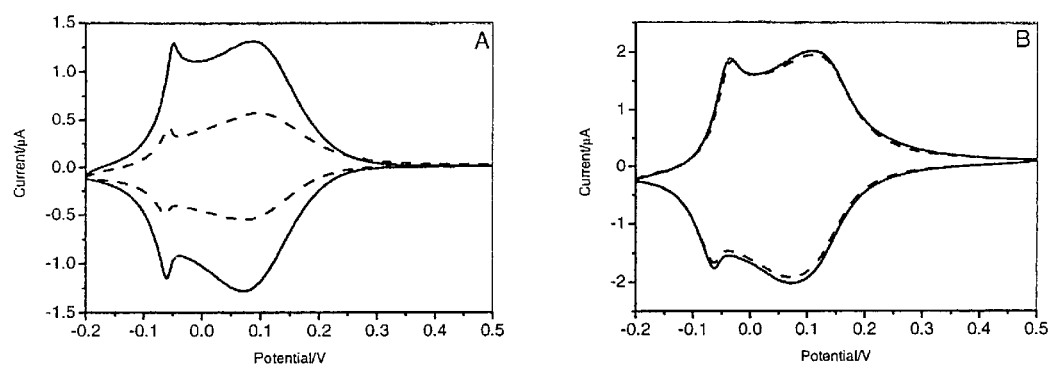

FIG. 4 depicts the FIA response of hypoxanthine on an RP modified biosensor in the absence of any polyaniline. It can clearly be seen that there is a decrease in the response with time to the hypoxanthine. This is due to the leaching of the RP. FIG. 5 also clearly shows the impact of the leaching of the RP, as the cyclic voltammogram of the biosensor without the polyaniline membrane becomes significantly smaller upon subsequent cycles. This is in contrast to the cyclic voltammogram B in FIG. 5, which shows little or no leaching upon repeated cycles.

Figure 6:
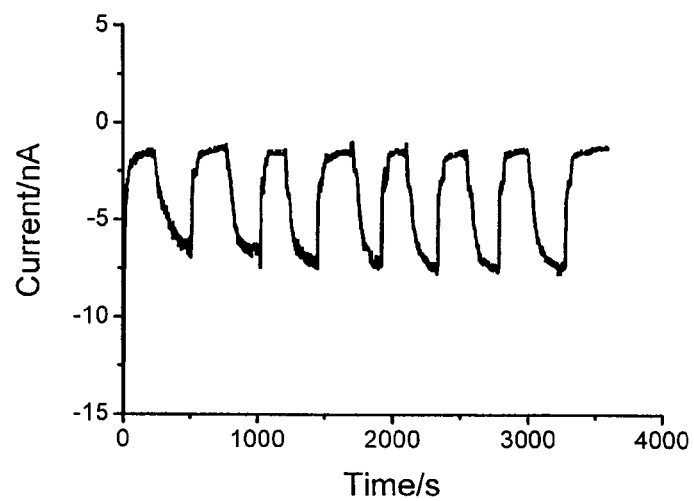

FIG. 6 further confirms this as the FIA response to hypoxanthine is consistent over time. The polyaniline substantially prevents the leaching of the RP in solution and also does not interfere with the electrochemistry.

Examples of polyaniline films in biosensors include Iwouoha E. I., et al. (Biosensors & Bioelectronics (1997), 12 (8): 749-761, Chois J. and Park S. M. (J. Electrochemical Soc. (2002), 149 (2): E26-E34) and Sun, et al. (J. Chem. Soc. Chem. Commun. (1990), 529-531).

Preferably at least a portion of the polyaniline is in its oxidised state. The presence of oxidised aniline appears to be particularly important in preventing leaching of the RP. The oxidised form of polyaniline is understood to be conductive.

Hence, preferably at least a portion of the polyaniline is oxidised. This may preferably be achieved, for example, by cycling the polyaniline layer with a positive voltage, for example, up to +1.3V to oxidise the polyaniline or derivative thereof.

While polyaniline is the preferred component of the membrane, other polyaniline derivatives comprising one or more non-polar substituents may also be used within the scope of the invention. By non-polar, we mean a functional group which possesses a low dipole moment value, and which is composed either of elements having nonpolar covalent bonds or polar covalent bonds that cancel each other out. Such substituents include, in particular, alkyl chains, preferably $C_1$-$C_{12}$ alkyl chains, and ethers, preferably containing $C_1$-$C_{12}$ alkyl chains. Any straight chain or branched alkyl chains are included, especially Me, Et, n-Pr, i-Pr, n-Bu, t-Bu, n-Pe and n-He.

Other polyaniline derivatives comprising one or more polar substituents, such as hydroxy or further amino groups (e.g. poly(aminophenols) or poly(diaminobenzenes)), or other substituted benzenes such as polyphenols or polypyrrole, do not function particularly well in the biosensors of the invention, as they either interfere in the electrochemistry or fail to prevent leaching.

Although RP modified biosensors are known in the art, they have not been employed in the detection of chemicals such as purines and derivatives thereof, such as hypoxanthine, ATP, adenosine and/or inosine. The prevention of leaching in microelectrodes is particularly important.

Preferably, the electrically conductive substrate comprises platinum or a platinum alloy, gold or a gold alloy, or carbon. More preferably, however, the substrate is platinum or a platinum-iridium alloy, such as containing a 90:10 ratio of platinum:iridium (weight:weight), or gold.

Preferably, the one or more biological materials in the matrix layer are enzymes. Preferably, the enzymes are independently selected from xanthine oxidase, glucose oxidase, lactate oxidase, cholesterol oxidase, galactose oxidase, glutamate oxidase, horse radish peroxidase, polyphenol oxidase, D-fructose dehydrogenase, L-glutamate dehydrogenase, alcohol dehydrogenase (such as methanol dehydrogenase), urease, uricase, lactate dehydrogenase, glutamic pyruvic transaminase, creatinase, sarcosine oxidase, glutaminase, nucleoside phosphorylase, ascorbate oxidase, cytochrome C oxidase, adenosine deaminase, D- or L-amino acid oxidase, tyrosinase, catalase, phosphoenolpyruvate kinase, glycerol kinase, glycerol-3-phosphate oxidase, phosphocreatine kinase, acetylcholine esterase, choline oxidase and/or cholinedehydrogenase. Other enzymes known in the art may also be used. The enzymes may be used separately or two or more together in the form of a cascade to measure one or more different substrates. Typically, such electrodes use an oxidoreductase which is capable of transferring an electron, via the RP, onto the electrode.

Preferably, the analyte is selected from the following analytes, which are given below, together with the preferred combination of enzymes used for their detection:

Glucose (glucose oxidase), lactate (lactate oxidase), cholesterol (cholesterol oxidase), galactose (galactose oxidase), glutamate (glutamate oxidase), hypoxanthine (xanthine oxidase), hydrogen peroxide (horse radish peroxidase), fructose (D-fructose dehydrogenase), glutamate (L-glutamate dehydrogenase), ethanol (alcohol dehydrogenase), methanol (methanol dehydrogenase), urea (urease), uric acid (uricase and horse radish peroxidase), lactate (L-lactate dehydrogenase and glutamic pyruvic transaminase), creatine (creatininase and creatinase and sarcosine oxidase), glutamine and glutamate (glutaminase or glutamate oxidase), adenosine (adenosine deaminase), ATP (glycol kinase or glycol-1,3-phosphate oxidase), and inosine (nucleoside phosphorylase).

Most preferably, the analyte is hypoxanthine, ATP, adenosine and/or inosine.

The ability to induce several enzymes at the same time improves the speed of production of the biosensor and the response obtainable by such biosensors.

Other enzymes include RNase, DNase, nuclease, ribonuclease and catalase. Active proteins, such as haemoglobin, myoglobin, collagen or tubulin may be added. Antibodies or fragments of antibodies, such as IgG, IgM or Fab or $F(ab^1)_2$ fragments may also be incorporated.

Most preferably, the biosensors contain an oxidoreductase enzyme, such as xanthine oxidase. The biosensor may additionally comprise nucleoside phosphorylase and/or adenosine deaminase. The enzyme may be glycerol kinase and glycerol kinase and glycerol-3-phosphate oxidase.

Xanthine oxidase may be used, for example, to detect hypoxanthine. If xanthine oxidase is used together with nucleoside phosphorylase, then the electrode may be used to detect xanthine, inosine and hypoxanthine. The addition of adenosine deaminase to the enzymes converts purines, such as adenosine, into inosine, therefore allowing the detection of purines such as adenosine by the sensor. Inosine, in turn, may be converted into hypoxanthine by nucleoside phosphorylase.

Finally, in the chain hypoxanthine is converted into uric acid and hydrogen peroxide by xanthine oxidase. It is the hydrogen peroxide that is detected by the substrate.

Using all three enzymes allows the detection of purines, such as adenosine to be detected, as well as inosine, hypoxanthine and xanthine. Using only nucleoside phosphorylase and xanthine oxidase means that inosine, hypoxanthine and xanthine may be detected. Alternatively, using only xanthine oxidase, hypoxanthine may be detected.

Preferably, an excess of xanthine oxidase compared with nucleoside phosphorylase is used. Preferably, approximately equal amounts of nucleoside phosphorylase and adenosine deaminase are used.

Most preferably the ratio of adenosine deaminase:nucleoside phosphorylase:xanthine oxidase is approximately 1:1:5, based on units of activity. This ratio has been found to be the optimal ratio for this sort of electrode.

ATP may be detected with glycerol kinase and glycerol-1,3-phosphate oxidase. Enzymatic amplification can be achieved by including creatine kinase as well.

Although purine biosensors are exemplified here, use of other enzymes and enzyme cascades of two or more enzymes may be used.

In the biosensor of the invention, hydrogen peroxide is preferably detected at the electrode as a product of the bio-reaction. The response correlates with the concentration of the substance to be detected. The RP, in its role as an electrochemical mediator, eliminates the overpotential of detecting the hydrogen peroxide directly on the surface of the biosensor electrode, which can cause other biochemical reagents (such as ascorbic acid or dopamine) to be co-oxidised, resulting in interferences in the results obtained.

The matrix may be any suitable matrix known in the art for entrapping biological materials for use in biosensors. Such matrices are discussed in, for example, Palmisano F. (2000) supra and WO 03/08721.

Enzymes may also be adsorbed onto the surface, for example, using glutaraldehyde to cross link the protein to a layer of bovine serum albumin (BSA). Alternatively, specific linkers known in the art, such as biotin, carboxy or amine groups, may be used to attach the enzymes.

In the present invention, RP is electrodeposited onto an electrode surface, and a matrix layer containing biological materials is then grown on the layer of RP. The RP is substantially unaffected by this. The matrix layer may be grown according to the method detailed in WO 2004/048603, incorporated herein by reference in its entirety.

A negative potential is preferred to grow the optimum matrix layer on RP. The layer can also be grown galvanostatically or at predetermined cathodic currents.

Preferably, the matrix layer is a sol-gel layer. However, the matrix layer can also comprise a hydrogel, polyvinyl, polyacrylamide, polypyrrole, and sugar-derivatised polypyrroles.

By sol-gel we mean a colloidal suspension of sol particles that is gelled to form a solid. A sol is made of colloidal particles which are, prior to gelling, dispersed in a fluid such as liquid. Typically, colloidal particles have a size of 1 nm to 100 nm diameter.

The sol-gel layer preferably comprises a sol of a silicon-containing compound, such as a silicate or a silane (such as an alkoxysilane), alumina, a ceramic oxide sol or a colloidal metal hydroxide.

U.S. Pat. No. 6,303,290 discloses a ceramic oxide colloidal sol which may be mixed with an acidified salt solution. Adding hydroxide to increase the pH causes the formation of a sol-gel. Using the method of the invention, instead of hydroxide, allows the electrodeposition of the sol-gel onto a substrate.

Accordingly, preferably the sol is a ceramic oxide sol, such as titanium oxide.

Zirconia ceramics may also be used as the sols. Gheorghies C. et al (Analele Stiintifice Ale Universitatii, Tomul XLV-XLVI, s. Fizica Starii Condensate (1999-2000) pages 268-275) discloses cathodic depositions of zirconia sol-gels. The electrical current was used to produce hydroxide ions which caused the deposition of the film. Preferably the acidified sol is $ZrO(NO_3)$.

Alternatively, the sol-gel layer can comprise a matrix of a hydrogel with polymers, such as polyvinyl, polyacrylamide or polypyrrole-based polymers, or sugar-derivatised polypyrroles, and their derivatives.

Preferably the sol is a silane. Preferably it has a general formula:

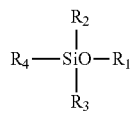

or $(R_9O)_3$—Si—$CH_2$—$CH_2$—Si—$(OR_9)_3$ where:
- $R_1$=straight chain, branched chain, cyclic, non-cyclic, saturated or non-saturated, substituted or non-substituted alkyl; substituted or non-substituted aryl; —$NR_5$; and —$COR_6$; the alkyl preferably contains 1, 2, 3, 4, 5 or 6 carbon atoms;
- $R_2$, $R_3$ and $R_4$ are independently selected from; straight chain, branched chain, cyclic, non-cyclic, saturated or non-saturated alkyl; —$COR_6$; —O-alkyl; and —O—$COR_6$; —$R_7R_8$; $R_7N(R_6)_2$ and $R_7NHR_6R_8$; preferably containing 1, 2, 3, 4, 5, or 6 carbon atoms;
- $R_5$=branched or non-branched cyclic or non-cyclic, saturated or non-saturated alkyl; or a benzyl group, preferably containing 1, 2, 3, 4, 5, or 6 carbon atoms;
- $R_6$=$C_1$ to $C_3$ alkyl;
- $R_7$=$C_1$ to $C_6$ alkyl, especially $C_1$, $C_2$ or $C_3$ alkyl;
- $R_8$=Epoxy, —$NH_2$ or —SH; especially

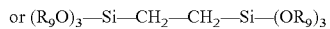

$R_9$=Straight or branched $C_1$ to $C_6$ alkyl, especially $C_1$, $C_2$ or $C_3$ alkyl.

Preferably $R_1$ is methyl, ethyl, propyl, —$NCHCH_2CH_3$, —$NC(CH_3)CH_2CH_3$,

—$NC(CH_3)CH_2CH(CH_3)_2$, —$COCH_3$ or

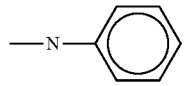

Preferably $R_2$, $R_3$ and $R_4$ are each independently methyl, ethyl, propyl, —O-methyl, —O-ethyl, —O-propyl, —$CHCH_2$, benzyl, —$OCOCH_3$, or aminoalkyl. Preferably, the aminoalkyl is aminopropyl, especially 3 aminopropyl.

Preferably the silanes are selected from:

Tetramethoxysilane (TMOS), tetraethoxysilane (TEOS), tetrapropoxysilane, methyltrimethoxysilane, methyltriethoxysilane, methyltris(methylethylketoxime)silane (MOS), methyltris(acetoxime)silane, dimethyldi(methylethylketoxime)silane, trimethyl(methylethylketoxime)silane, vinyltris(methylethylketoxime)silane (VOS), methyl tris(methylisobutylketoxime)silane, methylvinyldi(methylethylketoxime)silane, methylvinyldi(cyclohexanoneoxime)silane, vinyltris(methylisobutylketoxime)silane, phenyltris(methylethylketoxime)silane (POS), methyltriacetoxysilane and tetraacetoxysilane.

Preferably:
$R_1$=—$CH_3$, $R_2$=—$OCH_3$, $R_3$=—$OCH_3$ $R_4$=

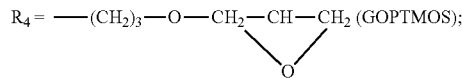

$R_1$=—$CH_3$, $R_2$=—$OCH_3$, $R_3$=—$OCH_3$, $R_4$=—$(CH_2)_3NH_2$ (APTMOS);
$R_1$=—$CH_2CH_3$, $R_2$=—$OCH_2CH_3$, $R_3$=—O—$CH_2CH_3$, $R_4$=—$(CH_2)_3NH_2$ (APTEOS);
$R_1$=—$CH_3$, $R_2$=—$OCH_3$ $R_3$=—$OCH_3$, $R_4$=—$(CH_2)_3SH$ (MPTMOS);
$R_9$=ethyl (Bis-TEOS); or $R_9$=methyl (Bis-TMOS)

Most preferably the silane is tetramethoxysilane (TMOS). Such silanes are known in the art and available commercially. Two or more silanes may be used.

Preferably a silane coupling agent is added. Such coupling agents contain a reactive group such as an amine, sulphydryl, oxy, acrylate, vinyl or chloro group. This may be added to the acidified sol suspension or to the neutralised sol suspension. These have been found to improve the stability of the film. Preferred coupling agents include:

3-Aminopropyl dimethyl methoxysilane (MMS)
Aminopropyltriethoxysilane
Aminopropyltrimethoxysilane
Aminopropylmethyldiethoxysilane
Aminopropylmethyldimethoxysilane
Aminoethylaminopropyltrimethoxysilane
Aminoethylaminopropyltriethoxysilane
Aminoethylaminopropylmethyldimethoxysilane
Diethylenetriaminopropyltrimethoxysilane
Diethylenetriaminopropyltriethoxysilane
Diethylenetriaminopropylmethyldimethoxysilane
Diethylenetriaminopropylmethyldiethoxysilane
Cyclohexylaminopropyltrimethoxysilane
Hexanediaminomethyldiethoxysilane
Anilinomethyltrimethoxysilane
Anilinomethyltriethoxysilane
Diethylaminomethyltriethoxysilane
(Diethylaminomethyl)methyldiethoxysilane
Methylaminopropyltrimethoxysilane
Bis(triethoxysilylpropyl)tetrasulfide
Bis(triethoxysilylpropyl)disulfide
Mercaptopropyltrimethoxysilane
Mercaptopropyltriethoxysilane
Mercaptopropylmethyldimethoxysilane
3-thiocyanopropyltriethoxysilane
Glycidoxypropyltrimethoxysilane
Glycidoxypropyltriethoxysilane
Glycidoxypropylmethyldiethoxysilane
Glycidoxypropylmethyldimethoxysilane
Methacryloxypropyltrimethoxysilane
Methacryloxypropyltriethoxysilane
Methacryloxypropylmethyldimethoxysilane
Chloropropyltrimethoxysilane
Chloropropyltriethoxysilane
Chloromethyltriethoxysilane
Chloromethyltrimethoxysilane
Dichloromethyltriethoxysilane
Vinyltrimethoxysilane Vinyltriethoxysilane Vinyltris(2-methoxyethoxy)silane Trimethoxysilyl aminopropyl aminoethyl triacetic acid -(MeO)$_3$SiCH$_2$CH$_2$CH$_2$N(CH$_2$COOH)CH$_2$CH$_2$N(CH$_2$COOH)$_2$ MMS has been found to be especially useful in adenosine sensors and stops the matrix becoming too dense. It is therefore preferably used for such sensors.

An electrical potential of about −900 to about −1500 mV, especially about −900 to about −1200 mV, is preferably used. The electrical potential may be applied for about 10 to about 120 seconds, especially about 20 to about 60 seconds, most preferably about 20 to about 40 seconds, depending on the thickness of sol-gel required.

Preferably the coupling agent is 3-aminopropyltrimethoxysilane (APTMOS).

Glycidylpropyltrimethoxysilane may also preferably be added to the neutralised sol-suspension.

The silane coupling agents preferably comprise one or more, especially two or more reactive groups, such as amine groups that cross-link the silane moieties.

Initial results show that the presence of mercaptan-containing silanes, such as MPTMOS, improve the sensitivity of biosensors produced by this technique, for example by lowering the sensitivity of the biosensor to contaminants in an assay mixture. They also improve the stability of biosensors in storage.

Initial results also show that the addition of bifunctional silanes, such as Bis-TEOS or Bis-TMOS, improve the stability and mechanical strength of biosensors.

Accordingly, the sol-gel is preferably obtained from a mixture comprising a mercapto-containing silane and/or a bifunctional silane.

The inventors have found that the sol-gel may be stabilised by the addition of one or more stabilisers such as a polyhydroxyalcohol. Examples include glycerol, polyethylene glycol (PEG) or polyvinyl alcohol; polysaccharides, such as dextran or chitosan; polyalkylene imine; or sugars, such as mannitol, gluconate, gluconolactone, trehalose, lactitol or sucrose, and benzylalkonium chloride (BAC).

Polyethyleneimine (PEI) may also be added.

Optionally, the biosensor according to the invention may also comprise a further layer of matrix, optionally without any biological material, which may be on top of the matrix layer containing the biological material(s).

Two or more biological materials, such as enzymes, may be used in a cascade; such enzymes may be mixed together and applied at the same time. Alternatively they may be applied as separate layers. A first layer is applied by switching on the electrical potential to form a first layer of matrix. The electrically conductive substrate is placed in a second neutralised matrix suspension containing a second enzyme, and a second matrix layer is applied by switching on an electrical potential again. The matrix used in the second suspension may be the same as or different to the first suspension.

Usually, stability, selectivity and sensitivity are the important factors in the development of a biosensor. As well as the pH stability shown in the inset in FIG. 3, the RP modified biosensor also shows a stable response to a substance in successive detection experiments. FIG. 6 shows an FIA response of a typical hypoxanthine biosensor to addition of 10 µM hypoxanthine solution. Over a one hour test, the biosensor exhibits a stable, reproducible response to the hypoxanthine.

As is known in the art, the activity of biological material(s) trapped within matrix layers of biosensors does not tend to fall. This is attributed to the rigidity and porosity of the sol-gel type matrices. Correspondingly, the activity of biological material(s) in the outer matrix layer of an RP modified biosensor is not affected by the RP layer during long term storage.

Figure 7:
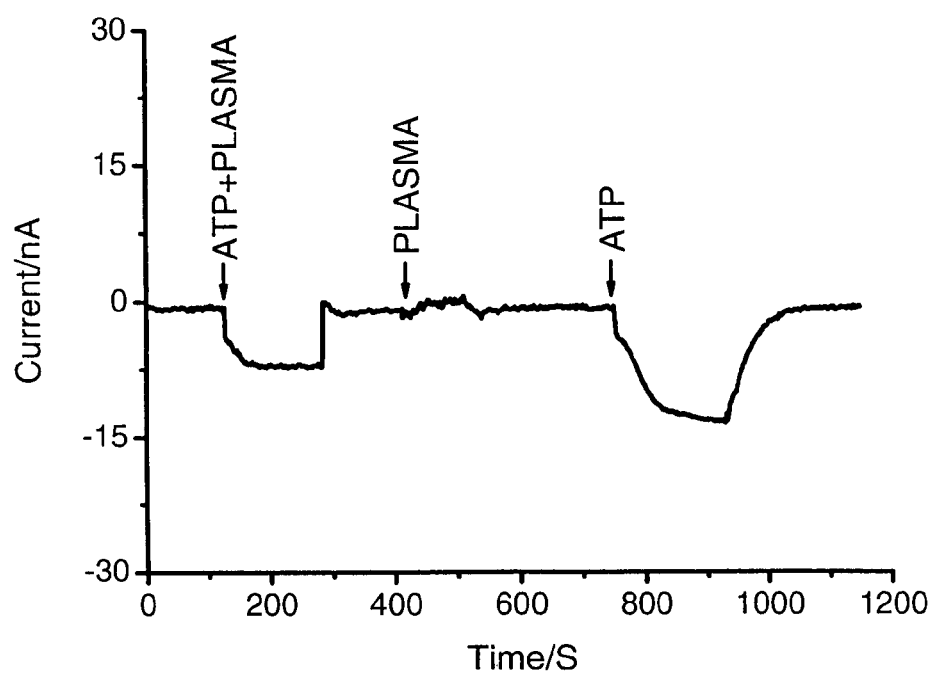

Plasma was employed to test the selectivity of the biosensor. FIG. 7 shows the amperometric response of the RP modified biosensor to ATP (40 µM), plasma, and mixtures of plasma and ATP (40 µM). It can be seen that the plasma gives hardly any interfering signal on the RP modified biosensor, indicating that the interferences are eliminated at a low operational potential. The RP modified biosensor of the invention therefore also exhibits good selectivity.

In normal biosensors, plasma interferes in the analysis of the substance which is being detected, as the components of plasma, such as urates and ascorbates generate large responses in the biosensors. Using the biosensor of the invention, these responses are greatly minimised due to the enhanced selectivity. Similarly, extremely reactive catechols at concentrations of 1 mM only generate responses which are between background and normal levels, and significantly less than those obtained from target substances.

Furthermore, the electrochemical behaviour of RP is substantially unaffected by the pH of the supporting electrolyte. This is shown in the cyclic voltammogram of FIG. 3 where the positions of the peaks I and II do not vary significantly with the change in pH. However, the stability and activity of the PB modified biosensors are seriously affected at alkaline pH, which restricts their use to only neutral and acidic solutions.

Figure 8:
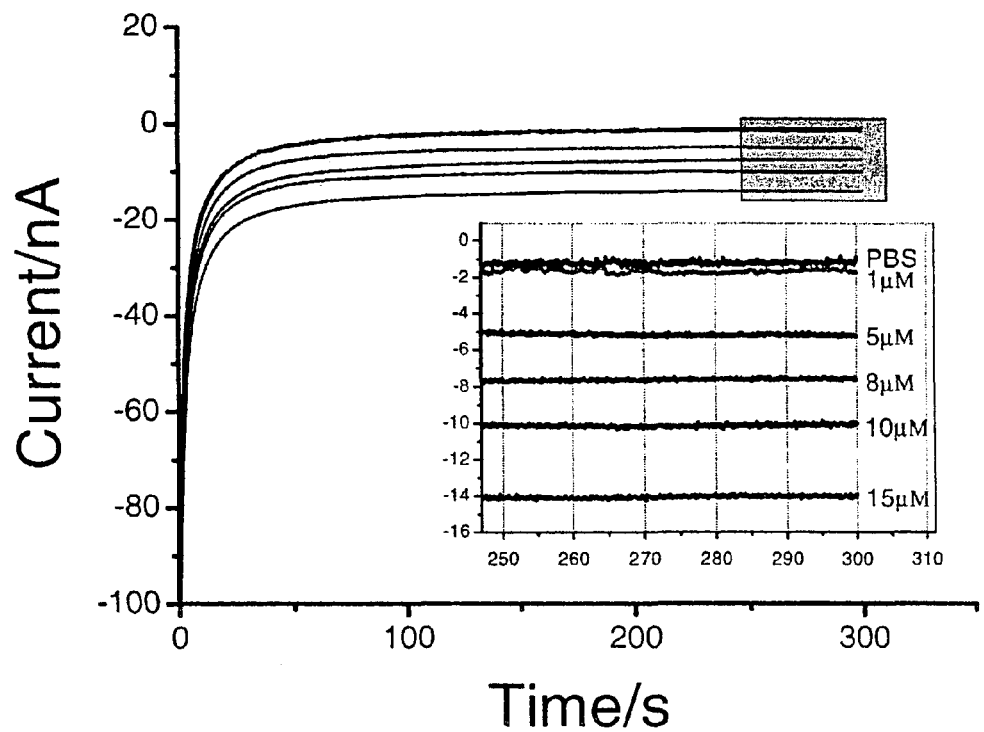

FIG. 8 depicts chrono-amperometric curves of a hypoxanthine biosensor obtained in a phosphate buffer with different concentrations of hypoxanthine, while the inset shows an enlargement of the selection. A sensitivity of 334.17 nA µM$^{-1}$ cm$^{-2}$ is obtained from the curves for the hypoxanthine biosensor.

Figure 9:
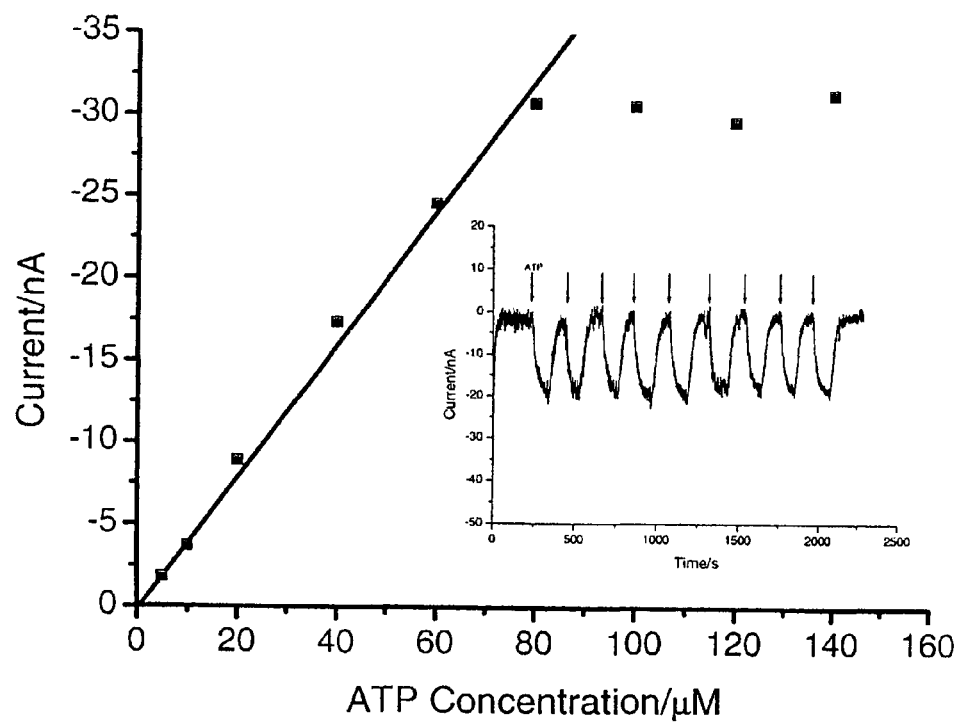

FIG. 9 shows a graph of current Vs. ATP concentration in the calibration of a typical ATP biosensor, while the inset shows the FIA response of a typical biosensor to ATP (40 µM) at an operating potential: 0 mV vs. Ag/AgCl. A clear, strong response to ATP is observed.

A further aspect of the invention provides a process for producing a biosensor according to the invention, comprising providing an electrically conductive substrate, the substrate preferably comprising platinum or a platinum alloy, gold or a gold alloy, or carbon, and depositing thereon;

(i) a first layer formed on the substrate, the first layer comprising Ruthenium Purple;

(ii) a second layer formed on the first layer, the second layer comprising polyaniline or a derivative thereof comprising one or more non-polar substituents; and (iii) a third layer formed on the second layer, the third layer comprising one or more enzymes trapped in a matrix or adsorbed onto the second layer.

Preferably, the process also involves heating and electrochemical cycling steps. More than about 20 cycles are preferably carried out, more preferably greater than about 30, and most preferably about 40 cycles. The cycling is preferably followed by heating for a period of time, e.g. overnight, preferably at greater than about 50° C., more preferably greater than about 60° C., still more preferably greater than about 70° C., and most preferably up to about 80° C.

Preferably the second layer is at least partially oxidised, for example, by cycling to around +1.3V, for example, for 4 to 7 cycles.

The substrate, polyaniline or its derivatives, matrix and biological materials may be as defined above for the first aspect of the invention.

The process of the invention is extremely controllable, with the layers obtained from the electrodeposition process being substantially the same each time. FIG. 1 shows a typical cyclic voltammogram monitoring the growth of RP on a gold electrode.

Additionally, the use of RP enables the use of particularly small biosensors. More specifically, biosensors which are approximately 50 μM in diameter and about 0.1 to about 2 mm in length are possible, preferably less than 25 μm in diameter and about 300 μm to about 2 mm long.

The operational stability of the biosensors of the invention is in the region of several hours, which is sufficient for the required detection experiments to be carried out.

According to a further aspect of the invention, the biosensor may be used as part of a foetal monitor.

As mentioned above, the ability to monitor hypoxanthine levels provides an indicator of a baby's levels of oxygen during birth and whether a caesarean section is necessary. The biosensor of the invention can be used to test drops of blood taken from the baby's scalp while it is still in the womb. The enzyme in the matrix layer is chosen in this case to be one which metabolises hypoxanthine, such as xanthine oxidase, and thus indicate how much is in the baby's blood.

The biosensor of the present invention requires less fine-tuning than existing tests for hypoxanthine, such as the blood pH test which needs to identify a pH shift of as little as 0.05, and would therefore be more reliable than the existing tests.

Use of the biosensor to detect chemicals such as purines such as hypoxanthine, ATP, adenosine and/or inosine, is also included within the scope of the invention. A method of detecting the amount of a chemical such as purine or a derivative thereof within a tissue or a bodily fluid, comprising exposing a biosensor according to the invention to a sample of the tissue in vivo or in vitro, and detecting an electrical current produced by the biosensor is also provided. Preferably, the tissue is blood, brain, rough or smooth muscle or cardiac tissue. The fluid may be saliva or urine.

A further aspect of the invention provides a kit comprising a biosensor according to the invention for detecting the presence and/or concentration of a chemical such as a purine or a derivative thereof. The kit may comprise means for recording a current from the biosensor in comparison with a reference electrode and may also comprise means for converting the current into an indication of the presence and/or concentration of the chemical to be analysed, such as purine or a derivative thereof. The kit may be used to detect one or more chemicals, e.g. purines, such as hypoxanthine, adenosine, ATP and/or inosine.

Alternatively, the biosensor may be incorporated into a larger biosensor for home use to enable an analyte, such as purine or a derivative thereof, to be monitored, for example in the saliva, blood or urine of a patient.

The invention will now be described by way of example only, with reference to the following Figures and Examples, which are intended to be illustrative only, and in no way limiting upon the scope of the invention.

FIG. 1. This shows the growth of an RP (ruthenium purple) layer on a gold electrode.

Figure 2:
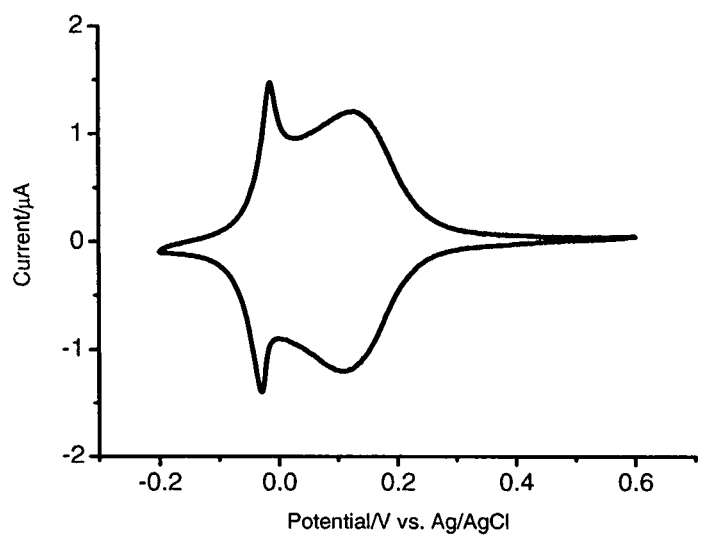

FIG. 2. This shows a cyclic voltammogram of an RP modified electrode in 0.1M sodium phosphate buffer solution.

Figure 3:
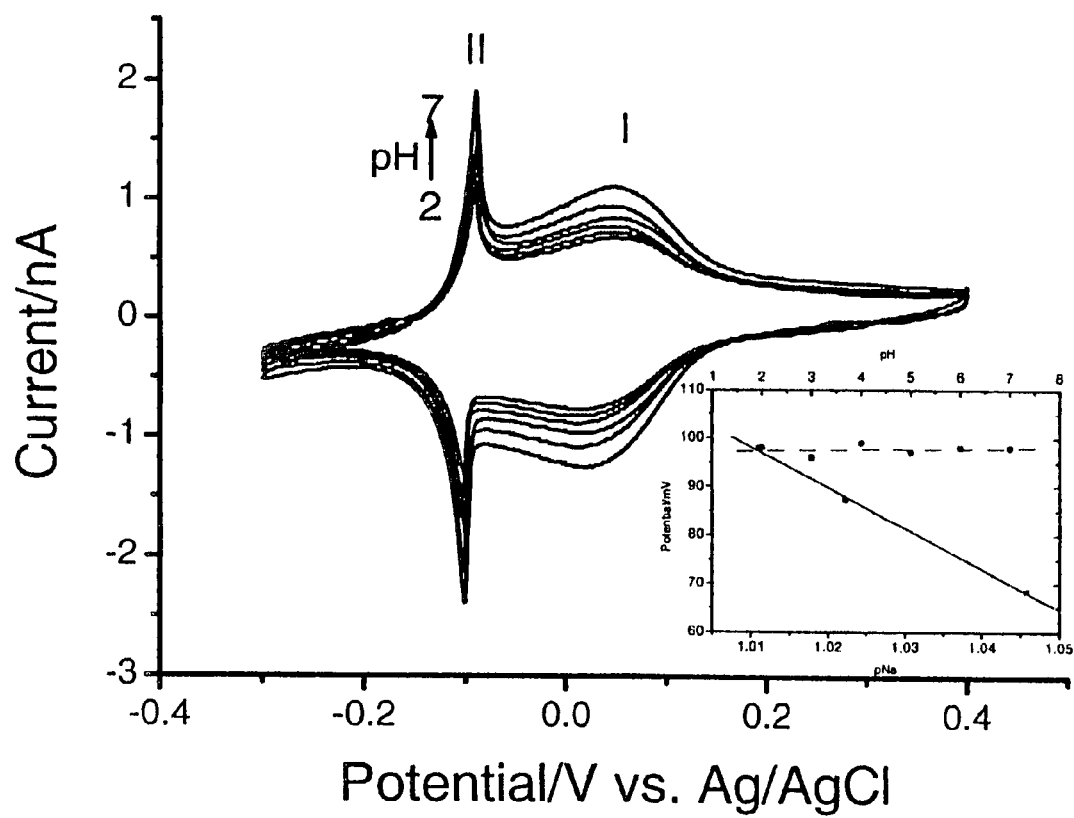

FIG. 3. This shows cyclic voltammograms of an RP modified biosensor in phosphate buffer at different pHs; the inset shows the effects of $Na^+$ ion concentration and pH on the reduction peak potential of peak II.

FIG. 4. This shows the flow injection analysis (FIA) response of hypoxanthine (10 μM) on an RP modified hypoxanthine biosensor without a polyaniline membrane. Applied potential: −50 mV vs. Ag/AgCl; supporting electrolyte is a phosphate buffer at pH 7.4.

FIG. 5. This shows a comparison of cyclic voltammograms of an RP modified biosensor without (A) and coated with (B) a polyaniline membrane scanned before (solid lines) and after (dashes) successive tests in 10 μM $H_2O_2$ for 1 hour.

FIG. 6. This shows the FIA response of RP and polyaniline modified hypoxanthine biosensor to hypoxanthine (10 μM). Applied potential: −50 mV vs. Ag/AgCl; supporting electrolyte is a phosphate buffer at pH 7.4.

FIG. 7. This shows the response of an ATP biosensor with RP and polyaniline to ATP (40 μM), plasma, and plasma+ATP (40 μM). Operational potential: 0 mV vs. Ag/AgCl; supporting electrolyte is a phosphate buffer at pH 7.4.

FIG. 8. This shows the response of a hypoxanthine biosensor comprising RP and polyaniline polarised at −50 mV vs. Ag/AgCl in a phosphate buffer with different concentrations of hypoxanthine.

FIG. 9. This shows the calibration of a typical ATP, RP and polyaniline biosensor. The inset shows the FIA response of a typical biosensor to ATP (40 μM). Operational potential: 0 mV vs. Ag/AgCl; supporting electrolyte is a phosphate buffer at pH 7.4.

Figure 10:
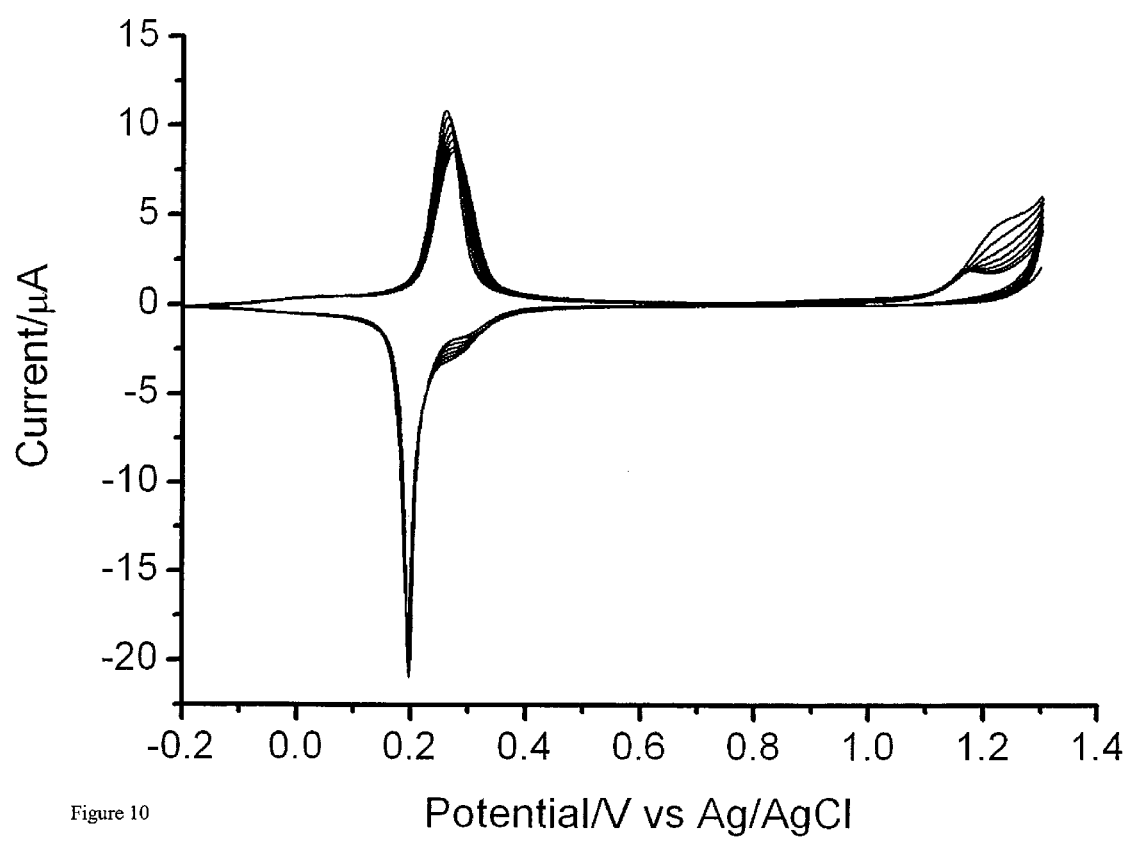

FIG. 10. This shows the coating of polyaniline onto a gold electrode surface by scanning CV in an acidic solution from −0.2 to 1.3V (VS AgCl) at a scan rate of 100 mV/s.

EXAMPLES

Apparatus

A CH1 660B potentiostat was used to electrochemically deposit the different polymers and test the biosensor. The biosensor was used in vivo with a potentiostat interfaced to a PC by an A to D converter board (Data Translation). In all cases an Ag/AgCl was used as reference electrode and a Pt counter electrode. The electrochemical cell for deposition consisted of a capillary of 1.5 mm diameter and 2 cm length.

Electrodeposition of RP on the Surface of a Gold Electrode:

In a three electrode system, a pre-treated working gold electrode is dipped into a mixture ($FeCl_3$ (1 mM)+KCl (40 mM, pH 2) and $K_4Ru(CN)_6$ (1 mM)+KCl (40 mM, pH 2), followed by electrochemical cycling from −0.2 to +0.7 V (vs. Ag/AgCl) for forty cycles at 50 mV/s (FIG. 1). The resulting RP modified electrode is heated at 80° C. overnight. In order to stabilise the RP membrane, electrochemical cycling is performed in a solution of $RuCl_3$.

Polyaniline, where used, was formed using 10 μm aniline plus 0.5M $H_2SO_4$+0.5M KCl cycling between −0.2 and +1.3V for 7 cycles at 100 mV/s. FIG. 10 shows the deposition of polyaniline.

Electrodeposition of the Sol-Gel Layer on the RP Modified Gold Electrode:

A pre-hydrolysed silane mixture was electrodeposited onto the surface of the RP modified electrode together with the appropriate enzyme(s). Different silane precursors are employed to obtain different sol mixtures, and different sol mixtures can be used to prepare different biosensor types.

A typical composition for an ATP biosensor includes TMOS (60 μl)+APTMOS (20 μl)+BISTMOS (20 μl)+GOPTMOS (20 μl)+Tris (100 μl)+glycerol (100 μl)+PEG (100 μl)+PEI (100 μl)+KCl (50 μl).

However, for an adenosine or a hypoxanthine biosensor, a typical composition includes TMOS (60 μl)+APTMOS (20 μl)+BISTMOS (20 μl)+GOPTMOS (20 μl)+MMS (20 μl)+

Tris (100 μl)+glycerol (100 μl)+PEG (100 μl)+PEI (100 μl)+ KCl (60 μl)+Ca(NO$_3$)$_2$ (100 μl)+BAC (10 μl).

Gel layers were preferably entrapped by electrodeposited at −0.9 to +1.3V or 6 to 8 μA for 10 to 30 seconds.

Hypoxanthine biosensors utilised xanthine oxidase as the enzyme. The ATP biosensor utilised a combination of glycerol kinase and glycerol-3-phosphate oxidase.

Typically 0.1-0.5 units of enzyme is used per microliter of the composition.

Biosensor Formation

Compared with the electrodeposition of a sol-gel layer onto a bare gold or platinum electrode surface, electrodeposition of a sol-gel layer onto the surface of the polyaniline layer on the RP modified gold electrode is more difficult. However, the most efficient method is to adjust either the operating potential (potentiostatic method) or current density (galvanostatic method). Typically, the biomolecule(s) can be entrapped within the gel layer by electrodeposition at about −0.9 to about −1.3 V, or about 6 to about 8 μA for 10-30 seconds.

The effect of adding polyaniline to the sensor is clearly demonstrated in the Figures. It shows that polyaniline improves the biosensor.

The invention claimed is:

1. A biosensor comprising:
   (i) an electrically conductive substrate;
   (ii) a first layer on the substrate, the first layer comprising Ruthenium Purple;
   (iii) a second layer on the first layer, the second layer comprising polyaniline or a derivative thereof comprising one or more non-polar substituents; and
   (iv) a third layer on the second layer, the third layer comprising one or more enzymes preferably trapped within a matrix or adsorbed onto the second layer.

2. A biosensor according to claim 1, wherein the non-polar substituents on the polyaniline derivative comprise one or more alkyl chains and/or ether groups.

3. A biosensor according to claim 1, wherein the non-polar substituents on the polyaniline derivative are selected from the group consisting of $C_1$-$C_{12}$ alkyl chains ether groups containing $C_1$-$C_{12}$ alkyl chains, and combinations thereof.

4. A biosensor according to claim 1, wherein the layer comprising the matrix is a sol-gel layer.

5. A biosensor according to claim 4, wherein the sol-gel layer comprises one or more silicon-based compounds, alumina, a ceramic oxide, a colloidal metal hydroxide.

6. A biosensor according to claim 1, wherein the matrix layer comprises a material selected from the group consisting of hydrogel, polyvinyl, polyacrylamide, polypyrrole, and sugar-derivatised polypyrroles.

7. A biosensor according to claim 1, wherein the matrix layer comprises one or more compounds selected from the group consisting of a silicate, a silane having the general formula:

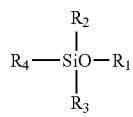

and (R$_9$O)$_3$—Si—CH$_2$—CH$_2$—Si—(OR$_9$)$_3$ where:
R$_1$=straight chain, branched chain, cyclic, non-cyclic, saturated or non-saturated, substituted or non-substituted alkyl; substituted or non-substituted aryl; —NR$_5$; and —COR$_6$;

R$_2$, R$_3$ and R$_4$ are independently selected from; straight chain, branched chain, cyclic, non-cyclic, saturated or non-saturated alkyl; —COR$_6$; —O-alkyl; and —O—COR$_6$; —R$_7$R$_8$; R$_7$N(R$_6$)$_2$, and R$_7$NHR$_6$R$_8$;

R$_5$=branched or non-branched cyclic or non-cyclic, saturated or non-saturated alkyl; or benzyl;

R$_6$=C$_1$ to C$_3$ alkyl;

R$_7$=C$_1$ to C$_6$ alkyl;

R$_8$=Epoxy, —NH$_2$ or —SH;

R$_9$=Straight or branched C$_1$ to C$_6$ alkyl.

8. A biosensor according to claim 7, wherein R$_1$ is methyl, ethyl, propyl, —NCHCH$_2$CH$_3$, —NC(CH$_3$) CH$_2$CH$_3$, —NC(CH$_3$)CH$_2$CH(CH$_3$)$_2$, COCH$_3$, or

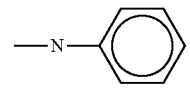

and R$_2$, R$_3$, and R$_4$ are each independently methyl, ethyl, propyl, O-methyl, O-ethyl, O-propyl, —CHCH$_2$, benzyl, or —OCOCH$_3$.

9. The biosensor of claim 7, wherein R$_1$ is an alkyl group having 1-6 carbon atoms.

10. The biosensor of claim 7, wherein R$_2$, R$_3$, and R$_4$ are each aminoalkyl.

11. The biosensor of claim 7, wherein R$_2$, R$_3$, and R$_4$ are each an alkyl group having 1-6 carbon atoms.

12. The biosensor of claim 7, wherein R$_5$ contains 1-6 carbon atoms.

13. The biosensor of claim 7, wherein R$_7$ is an alkyl group containing 1-3 carbon atoms.

14. The biosensor of claim 7, wherein R$_8$ is

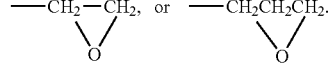

15. The biosensor of claim 7, wherein R$_9$ is an alkyl group containing 1-3 carbon atoms.

16. A biosensor according to claim 1, further comprising a silane coupling agent in the matrix layer.

17. A biosensor according to claim 1, wherein the one or more biological materials comprise one or more enzymes.

18. A biosensor according to claim 1, wherein the one or more enzymes permit the detection of purines and derivatives thereof.

19. A biosensor according to claim 18, wherein the purines and derivatives thereof are selected from hypoxanthine, adenosine, ATP and/or inosine.

20. A biosensor according to claim 1, wherein the one or more enzymes are selected from the group consisting of xanthine oxidase, nucleoside phosphorylase, glycerol kinase, glycerol-3-phosphate oxidase adenosine deaminase, and combinations thereof.

21. A biosensor according to claim 1, wherein the electrically conductive substrate comprises a material selected from the group consisting of platinum or a platinum alloy, and gold or gold alloy.

22. A biosensor according to claim 21, wherein the substrate comprises platinum or a platinum-iridium alloy, gold or a gold-alloy.

23. A foetal monitor comprising a biosensor according to claim 1.

24. A foetal monitor according to claim 23, wherein said foetal monitor detects hypoxanthine in an unborn child.

25. A kit for the detection of an analyte, comprising a biosensor according to claim 1.

26. The kit of claim 25, wherein said analyte is a purine or a derivative thereof.

27. A method of detecting one or more analytes in a sample of tissue or body fluid, comprising the steps of:
 providing the biosensor of claim 1;
 exposing said biosensor to a sample of tissue or body fluid; and
 detecting an electrical current produced by said biosensor.

28. The method of claim 27, wherein said one or more analytes are purines and derivatives thereof.

29. The method of claim 28, wherein said purines and derivatives thereof are selected from the group consisting of hypoxanthine, adenosine, ATP, inosinem, and combinations thereof.

30. A process for the preparation of a biosensor, comprising providing an electrically conductive substrate, the substrate comprising platinum or a platinum alloy, gold or a gold alloy, or carbon and depositing thereon;
 (i) a first layer formed on the substrate, the first layer comprising Ruthenium Purple;
 (ii) a second layer formed on the first layer, the second layer comprising polyaniline or a derivative thereof comprising one or more non-polar substituents; and
 (iii) a third layer formed on the second layer, the third layer comprising one or more enzymes preferably trapped in a matrix or adsorbed onto the second layer.

31. A process according to claim 30, further comprising electrochemically cycling and/or heating the Ruthenium Purple layer.

32. A process according to claim 31, wherein more than about 20 cycles are carried out and/or the Ruthenium Purple layer is heated to greater than about 50° C.

33. A process according to claim 32, wherein about 40 cycles are carried out and/or the Ruthenium Purple layer is heated to about 80° C.

* * * * *

UNITED STATES PATENT AND TRADEMARK OFFICE
CERTIFICATE OF CORRECTION

| | | |
|---|---|---|
| PATENT NO. | : 8,417,314 B2 | Page 1 of 1 |
| APPLICATION NO. | : 12/448625 | |
| DATED | : April 9, 2013 | |
| INVENTOR(S) | : Nicholas Dale and Faming Tian | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 286 days.

Signed and Sealed this
Second Day of July, 2013

Teresa Stanek Rea
*Acting Director of the United States Patent and Trademark Office*